United States Patent
Davis et al.

(10) Patent No.: US 6,631,353 B1
(45) Date of Patent: Oct. 7, 2003

(54) SONOMETRY AND DENSITOMETRY MEDICAL DIAGNOSTIC DEVICES ENABLED FOR PER-USE PATIENT EXAMINATIONS CHARGED VIA INTERNET CONNECTIONS TO FINANCIAL CARDS

(75) Inventors: David Davis, Sudbury, MA (US); Lorraine Schuft, Stow, MA (US)

(73) Assignee: Hologic, Inc., Bedford, MA (US)

( * ) Notice: Subject to any disclaimer, the term of this patent is extended or adjusted under 35 U.S.C. 154(b) by 626 days.

(21) Appl. No.: 09/591,002

(22) Filed: Jun. 9, 2000

Related U.S. Application Data

(60) Provisional application No. 60/138,477, filed on Jun. 10, 1999.

(51) Int. Cl.[7] .............................................. G06F 17/60
(52) U.S. Cl. ............................................ 705/2; 705/26
(58) Field of Search ................................. 705/2, 26, 59, 705/54; 700/275; 717/151; 235/381; 712/32

(56) References Cited

U.S. PATENT DOCUMENTS

| | | | |
|---|---|---|---|
| 5,696,906 A | 12/1997 | Peters et al. | |
| 5,755,228 A | 5/1998 | Wilson et al. | |
| 5,778,045 A | 7/1998 | von Stetten et al. | |
| 5,785,041 A | 7/1998 | Weinstein et al. | |

OTHER PUBLICATIONS http://www.emation.com/embedded/whitepapers/medial_wp.html, dated May 19, 2000, 2 pgs.
http://www.e-mation.com/embedded/casestudies/medical_devices.html, dated Jun. 9, 2000, 2 pgs.
http://www.e-mation.com/newsroom/companyhistory.html, dated Jun. 9, 2000, 1 pg.
http://www.e-mation.com.embedded/, dated Jun. 9, 2000, 2 pgs.
http://www.e-mation.com/products/, dated Jun. 9, 2000, 1 pg.
http://www.e-mation.com/newsroom/product_service_factsheet.html, dated Jun. 9, 2000, 2 pgs.

*Primary Examiner*—Le Hien Luu
(74) *Attorney, Agent, or Firm*—Cooper & Dunham LLP

(57) ABSTRACT

A system of fee-per-exam charging for the use of medical devices such as bone sonometers and x-ray densitometers. The customer or custodian of the device purchases a number of patient exams from the manufacturer or supplier of the equipment over an Internet connection with the company web site and receives a unique code that, when entered into the equipment, enables it to carry out the purchased number of patient examination and thereafter become disabled.

2 Claims, 1 Drawing Sheet

Figure 1:
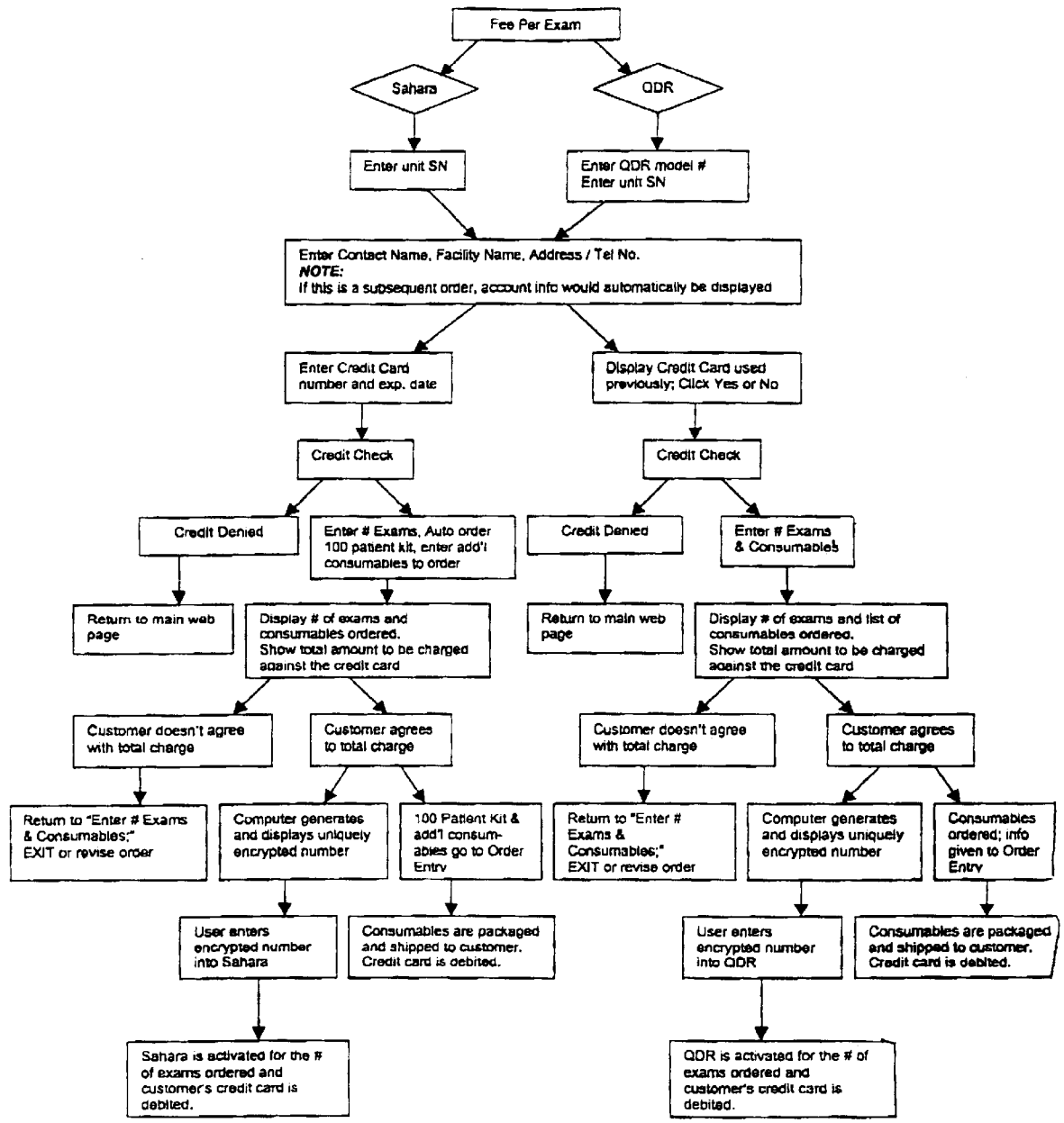

SONOMETRY AND DENSITOMETRY MEDICAL DIAGNOSTIC DEVICES ENABLED FOR PER-USE PATIENT EXAMINATIONS CHARGED VIA INTERNET CONNECTIONS TO FINANCIAL CARDS

REFERENCE TO RELATED APPLICATION

This patent specification is based on, claims the benefit of, and incorporates by reference Provisional Patent Application Ser. No. 60/138,477 filed on Jun. 10, 1999.

FIELD

The invention is in the field of medical diagnostic devices such as equipment for estimating properties of bone from ultrasound or x-ray measurements or for obtaining other medical diagnostic information, and in the field of methods of using such equipment. More specifically, the invention pertains to facilitating per-use charging for utilizing such equipment.

BACKGROUND

Typically, equipment of the type relevant to this patent specification is purchased or leased by the health care provider and no direct charge is made to the owner or lessee on a per-use basis. Some equipment may have provisions for keeping track of the cumulative in-use time, or number of patient examinations or calibration runs, and indirect charges or charges for consumables may be based thereon. It has been proposed to use special purpose cards serving as credit or debit cards to activate equipment and thus effectively charge on a per-use basis. See, e.g., commonly assigned patent application Ser. No. 09/241,973, now U.S. Pat. No. 6,234,959, which is hereby incorporated by reference herein. Still additionally, it has been proposed to use license keys to activate medical device software upon receipt of payment for products, and it has been proposed to track equipment via an Internet connection. Some examples of medical diagnostic devices of interest are disclosed in U.S. Pat. Nos. 5,778,045, 5,755,228, and 5,785,041, all hereby incorporated by reference herein. The ultrasound sonometer Sahara and the QDR series x-ray bone densitometers sold by the common assignee are non-limiting examples of such devices.

It is desirable in some cases to closely relate the costs of owning or operating medical diagnostic equipment to the patient examinations it carries out. One benefit can be that the equipment can be made in effect self-financing at least to some degree in that it can be purchased or leased at a lower cost and payments to the equipment supplier can be made as the equipment user is paid for patient examinations. Another is that cost can be tracked more easily, and service can be scheduled more easily by the entity servicing the equipment. Other advantages of charging the equipment operator on a fee-per-use basis will become apparent from the more detailed description below.

SUMMARY

This patent specification describes the use of a widely accessible network such as the Internet to effect charging on a per-use basis for patient examinations with medical equipment such as bone sonometry or densitometry devices and imaging equipment. Preferably, a charge is made via an Internet or some other network connection, to a debit or credit card or some other financial card, or to an account. This charge authorizes a certain number of patient examinations or other procedures with the device. Such authorization enables the device for the prescribed number and type of procedures and then disables it.

In a preferred embodiment, a medical diagnostic device is connected as needed to a remote fee-per-use administrative center such as a server location. Such capability often is built into such medical diagnostic devices for other purposes, such as service diagnostics or remote servicing. If not already available, it can be implemented readily, using commercially available hardware and software added to the computer that typically is included in some form in the medical diagnostic device, either as a personal computer or an embedded data processing and control device. The existing or added facilities for such a connection typically comprise a modem or some other interface to a communication link such as a telephone line, and appropriate software as known in the art.

Via the Internet or similar connection, a medical device user or operator supplies to the central facility the information needed to purchase a certain number of patient examinations or other procedures. This information can include the identity of the machine and the user or operator, the desired number of procedures, and charging information such as the number of a credit or debit card or some other financial card or an account that can be charged or credit that can be used. Following a check of the information and an authorization for charging, such as the authorization typically secured by merchants when credit cards are used, the administration site declines or provisionally accepts the request. It may decline for reasons such as because the financial card has expired or because the identity of the requester or the diagnostic machine does not match the records, or for some other reason. If the administration facility provisionally accepts the request, it can display the information for verification by an employee and/or the requester, so that any changes and adjustments can be made before the transaction is finalized. Once that transaction is finalized, after the requester has confirmed the purchase of a certain number of procedures and possibly other goods or services, such as consumables, the administration facility generates an encrypted code unique to the purchase. If any goods or services in addition to patient examinations or other protocols with the medical device were purchased, appropriate arrangements are made for sending the goods or supplying the services. The financial card or account of the purchaser is debited for the amount of the purchase.

The unique, encrypted code that was generated for the purchase enables the medical device to perform the designated number of protocols. For example, it is supplied to the user or operator of the machine, who manually enters it through a keyboard or some other interface into the machine. Through suitable preinstalled programming, the machine responds by enabling itself to carry out the purchased type and number of protocols. For example, the authorized protocols can be patient examination, and the machine will disable itself after the purchased number has been carried out, but can continue to carry out calibration runs with phantoms.

DRAWING

FIG. 1 illustrates an example of a flowchart of steps comprising a non-limiting example of effecting per-use charging for medical equipment in the case of a sonometer tradenamed Sahara and an x-ray bone densitometer family tradenamed QDR, both available from Hologic, Inc. of Bedford, Mass.

DETAILED DESCRIPTION OF AN EXAMPLE

In the case of a customer such as a purchaser or lessee or custodian of medical equipment such as, without limitation, a Sahara sonometer or a QDR x-ray bone densitometer, the equipment can be configured to permit an examination, such as a patient examination, only upon the successful processing of an appropriate authorization. One example of such authorization is a response to charging a fee for a patient examination so that the equipment can be operated on a Fee Per Exam basis. The system can be implemented through a company's Web Site, for example the Internet Web Site of a Company that manufactured or otherwise supplied the medical equipment.

To purchase exams, a customer accesses the Company's Web Site via the Internet, and connects to a Fee Per Exam section of the Web Site. As illustrated in the flow chart of FIG. 1, the customer is prompted to enter a credit or debit card number and expiration date to purchase a fixed number of exams and consumables. Once this information is entered and a credit check is performed, the customer selects the number of exams to purchase, answering an appropriate question through the Internet connection. This may be in increments of 50, or some other number of exams. With each Fee Per Exam order, a consumables package can be automatically sent to the customers, such as a Sahara 100 Patient Supply Kit. The customer can elect to purchase additional supplies, in the same general manner. After the computer at the Company's Web Site receives and processes this information, it generates a uniquely encrypted number. Sahara and QDR software is modified such that when this encrypted number is entered into either device, it activates the device, making it fully operational and the customer is able to perform the requested number of exams. Each code is only able to be used once to activate the device. The device automatically shuts down to prevent patient examinations after all of the exams for which the customer has paid a fee have been performed.

In general, the process that a customer goes through is outlined in the flow chart of FIG. 1 and is also noted below:

1. Customer selects "Fee Per Exam" from the Company's main web page.

2. Customer then selects "Sahara" or "QDR."

3a. If Sahara was selected, the customer then enters the serial number of the device.

3b. If QDR was selected, the user would enter the model number and serial number of the device.

4. If this was the first time that the customer was ordering exams, then the customer is prompted to enter the customer's facility name, contact name, address and telephone number.

5a. If the customer had used the "Fee Per Exam" feature before, then the demographic and credit card data would be displayed to the customer once the unit's serial number was entered into the system.

5b. If this was the first time that the customer was purchasing exams via the Company's web site, then the customer would be prompted to enter a credit or debit card number and expiration date.

6. A credit check is automatically performed on-line by the Company.

7a. If credit is denied, the customer is returned to the Company's main web page.

7b. If credit is approved, then the customer is prompted to select the number of exams to purchase. An order for a Sahara 100 Patient Supply Kit is automatically processed. If additional consumables are required, then the customer would enter the order at this point in time.

8. The customer's order is then displayed including the number of exams, the quantity of consumables plus the total amount to be debited from the credit or debit card.

9. The customer indicates agreement or disagreement with this total amount.

10a. If the customer does not agree with the total amount of the order, the customer is returned to the page where the number of exams to be purchased and the additional quantity of each type of consumable ordered were specified. From there, the customer can EXIT or revise the order. If the customer revises the order, then the process begins again from #7b noted above.

10b. If the customer agrees with the total amount of the order, then a unique, encrypted number is generated through the Company's Web Site computer and displayed to the customer. The customer's consumable order is placed in the Company's order entry system and forwarded to the shipping department.

11. The customer or the equipment user enters the encrypted number into either the Sahara or the QDR.

12. The Sahara or QDR is activated for the number of exams purchased; the customer's credit or debit card is debited for the exams.

13. The Sahara 100 Patient Supply Kit and any additional consumables are packaged and shipped to the customer; and the credit or debit card is debited for the consumables.

A similar system can apply to other medical devices, consumables, and services of the type available from the Company.

The advantages of the system described herein include:

Easy to administer
Convenient for the Company and the customer or end-user
Eliminates manual tracking of exams performed
Automatic system shut-down upon completion of the number of exams purchased
No need for on-site monitoring visit by the Company's employee
Enables pre-payment for exams via credit or debit card
Prevents mis-use by customers If the Sahara and QDR devices are not provided with mechanism to suspend operation of the unit after a finite number of exams have been performed, as described above, then a Fee Per Exam Program for Sahara can require manually monitoring the number of exams performed on a periodic basis. This would require the Company's employee to track and administer. Sahara has a counter incorporated in it that can be printed out upon request to determine the number of exams performed. This would have to be routinely tracked by an on-site visit by the Company's representative to ensure the integrity of the program. As this counter is not re-set to zero, the Company would need to keep a running tally of the number exams on any given unit as it moved from one customer to another. In addition, if the Sahara unit is not configured to cease operation after the customer had performed the number of tests he or she purchased as described above, it would be possible for customers to take advantage of this and perform more exams than they had purchased. For this reason, a manual Fee Per Exam program of this nature would require close scrutiny by the Company's personnel.

In contrast, authorizing Sahara and/or QDR via the Internet to carry out a purchased number of patient exams would be convenient for both the customer or other end-user and the Company. Using a uniquely encrypted number for each purchase of exams will prevent abuse of the program. Confirmation of the customer's credit or debit card, or other source of funds, will ensure payment of exams.

What is claimed is:

1. A method of enabling medical equipment to perform patient examinations on a fee-per-exam basis comprising the steps of:

establishing an Internet connection between a customer site and a company web site;

entering an order at the customer site identifying the equipment for which patient exams are to be purchased and a number of exams and any consumables that are desired to be purchased, and transmitting information identifying the order from the customer site to the company web site;

performing a financial check to determine whether to accept the order and, if the order is accepted, generating a unique code indicative of the order including a number of exams for which the equipment is to be enabled; and entering the unique code into the equipment to enable the equipment to perform a number of patients exams related to the order that resulted in the generation of the unique code.

2. A method of enabling medical equipment to perform a specified number and type of patient protocols on a fee-per-exam basis comprising the steps of:

establishing a wide area network connection between a customer site and a remote administrative site;

supplying the administrative site with order information from the customer site over the wide area network, identifying the equipment for which the patient protocols are to be purchased and a number or protocols to be purchased and identifying any consumables that are desired to be purchased;

performing a financial check to determine whether to accept the order and, if the order is accepted, debiting an account related to the customer and generating an encrypted unique code related to the order, said code including a number of patient protocols for which the equipment is to be enabled;

transmitting the unique code to the customer location;

entering the unique code into the equipment and thereby enabling the equipment to perform a number of patients protocols related to the order that resulted in the generation of the unique code; and disabling the ability of the equipment to carry out the patient protocols after the number of purchased patient protocols has been carried out.

* * * * *